United States Patent
Kumar et al.

(10) Patent No.: US 9,760,798 B2
(45) Date of Patent: Sep. 12, 2017

(54) ELECTRONIC COASTER FOR IDENTIFYING A BEVERAGE

(71) Applicant: Wipro Limited, Bangalore (IN)

(72) Inventors: Vijay Kumar, Bangalore (IN); Saurav Labana, Chandigarh (IN)

(73) Assignee: WIPRO LIMITED, Bangalore (IN)

( * ) Notice: Subject to any disclaimer, the term of this patent is extended or adjusted under 35 U.S.C. 154(b) by 0 days.

(21) Appl. No.: 15/066,187

(22) Filed: Mar. 10, 2016

(65) Prior Publication Data

US 2017/0213104 A1      Jul. 27, 2017

(30) Foreign Application Priority Data

Jan. 21, 2016    (IN) .............................. 201641002347

(51) Int. Cl.
    *G06K 9/00*    (2006.01)
    *A47G 23/03*   (2006.01)
    (Continued)

(52) U.S. Cl.
    CPC ........... *G06K 9/6202* (2013.01); *A47G 23/03* (2013.01); *G01N 21/00* (2013.01);
    (Continued)

(58) Field of Classification Search
    CPC .. A47G 23/03; A47G 23/0309; A47G 23/032; A47G 23/14; G06T 5/50; G06K 2009/4657; G01N 21/00
    See application file for complete search history.

(56) References Cited

U.S. PATENT DOCUMENTS

| 6,018,403 A  | * | 1/2000 | Shirakura | ............ | G03H 1/0408 |
|  |  |  |  |  | 359/23 |
| 7,353,136 B2 | * | 4/2008 | Vock | .................... | A43B 3/0005 |
|  |  |  |  |  | 702/173 |

(Continued)

FOREIGN PATENT DOCUMENTS

| GB | 2488572 | 9/2012 |
| KR | 20100046480 | 5/2010 |
| WO | WO 2013/086372 | 6/2013 |

OTHER PUBLICATIONS

Meyers, J.E., et al., "A Study of the Effectiveness of Commercially Available Drink Test Coasters for the Detection of "Date Rape" Drugs in Beverages", *Journal of Analytical Toxicology*, vol. 28, Jan. 1, 2004, pp. 685-688.

(Continued)

*Primary Examiner* — Utpal Shah
(74) *Attorney, Agent, or Firm* — Finnegan, Henderson, Farabow, Garett & Dunner LLP (57) ABSTRACT

The present disclosure discloses an electronic coaster, comprising at least one first imaging sensor to capture at least one first image of a beverage present in a beverage holder placed on the electronic coaster, at least one second imaging sensor to capture at least one second image of ambience around the electronic coaster and a computing unit to receive the at least one first image and the at least one second image, process spectrum of the at least one first and second image for obtaining spectral signature of the beverage and compare the spectral signature of the beverage with predefined spectral signature of plurality of beverages to identify type of the beverage.

16 Claims, 5 Drawing Sheets

(51) Int. Cl.
- *G06T 5/00* (2006.01)
- *G06K 9/62* (2006.01)
- *G06T 7/00* (2017.01)
- *G06F 17/30* (2006.01)
- *G06T 5/50* (2006.01)
- *G01N 21/00* (2006.01)
- *G06K 9/46* (2006.01)

(52) U.S. Cl.
CPC .... *G06F 17/3028* (2013.01); *G06F 17/30256* (2013.01); *G06F 17/30259* (2013.01); *G06F 17/30262* (2013.01); *G06K 9/00892* (2013.01); *G06T 5/50* (2013.01); *G06T 7/0004* (2013.01); *G06K 2009/4657* (2013.01); *G06T 2207/30128* (2013.01)

(56) References Cited

U.S. PATENT DOCUMENTS

| | | | | |
|---|---|---|---|---|
| 8,335,550 | B2* | 12/2012 | Segman | A61B 5/0059 356/300 |
| 9,643,091 | B2* | 5/2017 | Vock | A63F 13/798 |
| 2006/0026971 | A1 | 2/2006 | Sharpe | |
| 2006/0052983 | A1 | 3/2006 | Vock et al. | |
| 2006/0143645 | A1* | 6/2006 | Vock | A43B 3/00 725/9 |
| 2007/0024465 | A1 | 2/2007 | Howell et al. | |
| 2008/0077471 | A1* | 3/2008 | Musgrove | G06Q 30/02 705/7.29 |
| 2010/0138166 | A1 | 6/2010 | Do et al. | |
| 2011/0053283 | A1 | 3/2011 | Hood et al. | |
| 2013/0014648 | A1* | 1/2013 | Rognon | A47J 31/3623 99/280 |
| 2014/0141837 | A1* | 5/2014 | Pinapala Venkata | H04M 1/72522 455/556.1 |
| 2014/0310112 | A1* | 10/2014 | Hyde | G06Q 50/12 705/15 |
| 2015/0168365 | A1 | 6/2015 | Connor | |
| 2016/0081506 | A1* | 3/2016 | Bizzarri | A47G 23/03 248/346.11 |
| 2017/0103419 | A1* | 4/2017 | Gibson | G06Q 30/0257 |

OTHER PUBLICATIONS

Extended European International Search Report issued in the European Patent Office in counterpart European Application No. 16158820.7, dated Jul. 7, 2017, 9 pages.

* cited by examiner

ELECTRONIC COASTER FOR IDENTIFYING A BEVERAGE

TECHNICAL FIELD

The present disclosure relates to a device and a method for beverage recognition. More specifically the disclosure illustrates an electronic coaster for identifying a beverage type based on spectral analysis of an image of the beverage.

BACKGROUND

In general, people tend to socialize over beverages. In a typical scenario, when a beverage is emptied, people seek an attendant's help to refill the beverage or place an order for a different beverage. For the person, it may seem annoying to repeatedly reach out to the attendant for placing an order. For example, in a restaurant or bar, a user may place an order for a drink. Soon after the drink is consumed, the user has to contact concerned person to order the same type of drink or a different type of drink. The user may be displeased by frequent interaction with the attendant. Also, when a different attendant attends the user, the attendant may not know the type of beverage the user has consumed. Also, the attendant cannot suggest any beverage without prior knowledge of the users' choice of beverage.

Current technology provides ways to place an order through a user interface associated with a table the user is seated in. However, the user may have to constantly make use of the user interface to place a new order. In some scenarios, for example a bar, a user may consume alcohol and may not be able to use the user interface efficiently. In another example, an aged user may not be able to use the complex features presented in the user interface. Also, there does not exist a device to intelligently identify the beverage consumed by a user and inform concerned personnel to attend the user on requirement.

SUMMARY

Disclosed herein is an electronic coaster for identifying a beverage type. The electronic coaster analyses spectral signature of the beverage and identifies the beverage type based on the performed analysis. The electronic coaster thus helps an attendant to provide service to a user on requirement.

In an embodiment, the present disclosure shows an electronic coaster, comprising at least one first imaging sensor to capture at least one first image of a beverage present in a beverage holder placed on the electronic coaster, at least one second imaging sensor to capture at least one second image of ambience around the electronic coaster and a computing unit to receive the at least one first image and the at least one second image, process spectrum of the at least one first and second image for obtaining spectral signature of the beverage and compare the spectral signature of the beverage with predefined spectral signature of plurality of beverages to identify type of the beverage.

In an embodiment, the present disclosure illustrates a method for identifying a beverage by an electronic coaster, comprising capturing, by at least one first imaging sensor, at least one first image of a beverage present in a beverage holder placed on the electronic coaster, capturing, by at least one second imaging sensor, at least one second image of ambience around the electronic coaster, receiving, by a computing unit, the at least one first image and the at least one second image, processing spectrum of the at least one first and second image for obtaining spectral signature of the beverage and comparing the spectral signature of the beverage with predefined spectral signature of plurality of beverages to identify type of the beverage.

In an embodiment, the present disclosure relates to a non-transitory computer readable medium including instructions stored thereon that when processed by at least one processor of a computing unit cause a device to perform operations comprising capturing at least one first image of a beverage present in a beverage holder placed on the electronic coaster, capturing at least one second image of ambience around the electronic coaster, receiving the at least one first image and the at least one second image, processing spectrum of the at least one first and second image for obtaining spectral signature of the beverage and comparing the spectral signature of the beverage with predefined spectral signature of plurality of beverages to identify type of the beverage.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Embodiments of the present disclosure relate to an electronic coaster for identifying type of beverage present in a beverage holder placed on the electronic coaster. The identified beverage type is then communicated to concerned personnel, thus enabling timely service to a user consuming the beverage.

Figure 1:
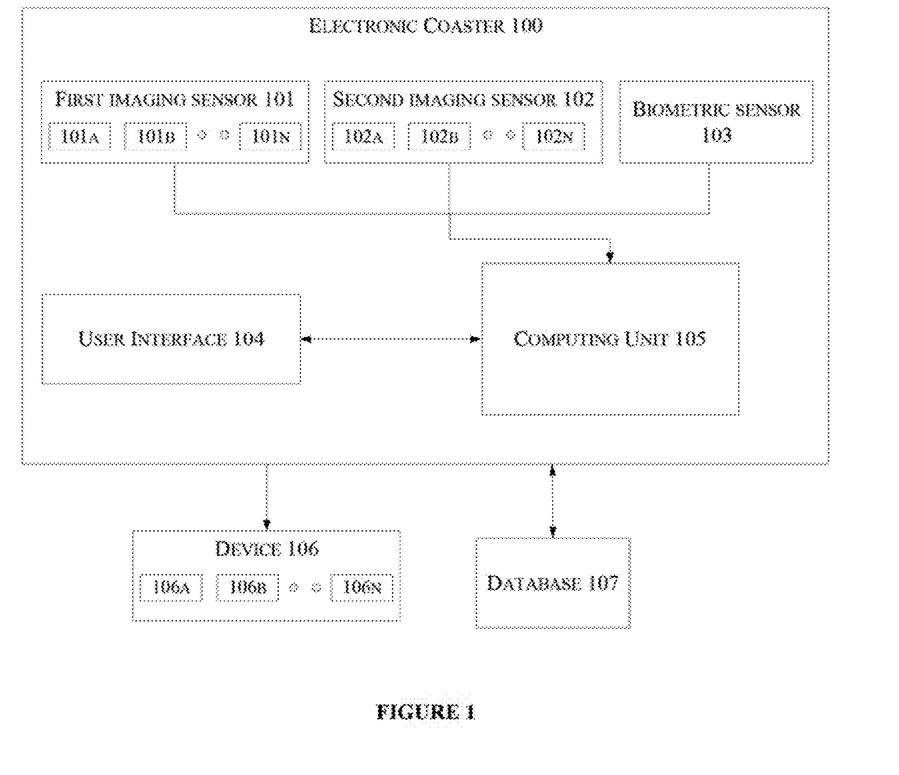
FIG. 1 illustrates an exemplary block diagram of an electronic coaster in accordance with some embodiments of the present disclosure.

FIG. 1 illustrates an electronic coaster 100 comprising a first imaging sensor 101A, a first imaging sensor 101B, . . . , a first imaging sensor 10N, collectively represented as at least one first imaging sensor 101. The electronic coaster 100 further comprises a second imaging sensor 102A, a second imaging sensor 102B, . . . , a second imaging sensor 102N, collectively represented as at least one second imaging sensor 102. Further, the electronic coaster 100 comprises a computing unit communicatively coupled to the at least one first imaging sensor 101 and at least one second imaging sensor 102. The at least one first imaging sensor 101 captures at least one first image of a beverage present in a beverage holder placed on the electronic coaster 100. The at least one second imaging sensor 102 captures at least one second image of ambience around the beverage holder. Then, the computing unit 105 receives the at least one first and second image to determine light spectrum of the at least one first and second image. The determined light spectrum is then processed by the computing unit 105 to obtain a spectral signature of the beverage. Spectral signature of a beverage may be defined as radiation reflected by the beverage or refracted through the beverage, as a function of wavelength of light used in the radiation. In an embodiment, a database 107 accessible by the electronic coaster 100 is configured with predefined spectral signature of plurality of beverages. Lastly, the computing unit 105 compares the spectral signature of the beverage with the predefined spectral signature of plurality of beverages to identify the type of beverage.

In an embodiment, the electronic coaster 100 further comprises a user interface 104. A user can interact with the electronic coaster 100 through the user interface 104. The user interface 104 receives one or more inputs from the user. In an embodiment, the one or more inputs may include, but are not limited to, user registration details, choice of beverage, amount of the beverage, budget, etc. The identified beverage type is displayed to the user through the user interface 104. In an embodiment, the database 107 also stores the one or more inputs provided by the user. The database 107 can be connected to the electronic coaster 100 through one of wired network or wireless network.

In an embodiment, the electronic coaster 100 further comprises a biometric sensor 103 to identify one or more users associated with the electronic coaster 100. Upon identifying the user, the electronic coaster 100 may intimate the concerned personnel to provide one or more services to the user based on the one or more inputs stored in the database 107.

In an embodiment, the computing unit 105 is configured to transmit the identified beverage type to at least one of device 106A, a device 106B, . . . a device 106N communicatively associated with the electronic coaster 100. In the present disclosure, the device 106A, the device 106B, . . . the device 106N are collectively represented as one or more devices 106. Here, the one or more devices 106 are one of, but not limited to, a mobile phone, tablet, PDA or any other computing device. Further, the identified beverage type may be transmitted by one of wired interface and wireless interface. Furthermore, the transmitted beverage type can be accessed by the concerned personnel through the one or more devices 106. Here, the concerned personnel may be the user, an attendant, a relative of the user, a person accompanying the user or any person associated with the user.

Figure 2:
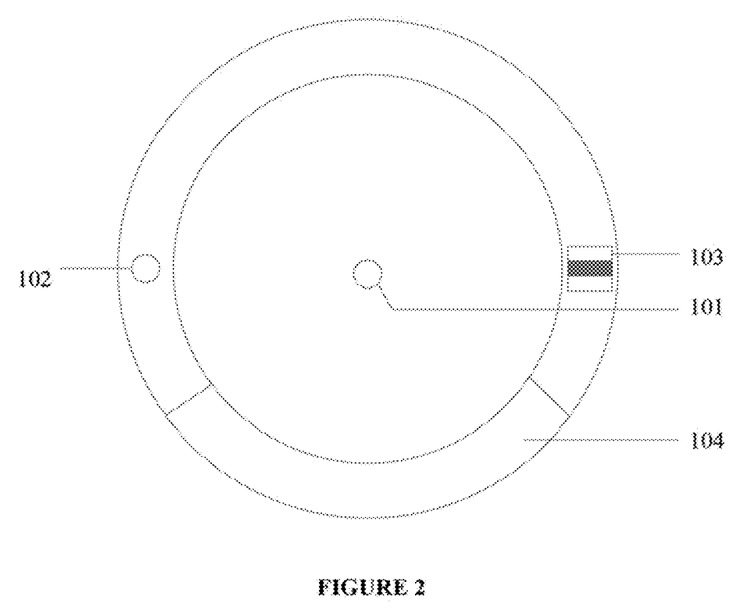
FIG. 2 shows a structural diagram of an electronic coaster in accordance with some embodiments of the present disclosure.

FIG. 2 illustrates a structural representation of the electronic coaster 100. The figure illustrates integration of sensors with the electronic coaster 100. The electronic coaster 100 may be made up of a hard enclosure to house one or more sensors (101 and 102), circuitry etc. The hard enclosure may be one of plastic, metal, fibre, etc., or any material durable enough to hold a beverage holder. In an embodiment, the hard enclosure can be a waterproof material. The at least one first imaging sensor 101 is configured in the electronic coaster 100 such that it is positioned beneath the beverage holder to capture at least one first image of the beverage present in the beverage holder. The at least one second imaging sensor 102 is configured to capture at least one second image of ambience around the beverage holder. The at least one second imaging sensor 102 is positioned in a way not to be covered by the beverage holder. The at least one first imaging sensor 101 and the at least one second imaging sensor 102 are one of Red Green Blue (RGB) sensors, hyper-spectral sensors or any type of imaging sensors capable to assist in identifying the type of beverage.

In an embodiment, the biometric sensor 103 is installed in the electronic coaster 100 to identify one or more users associated with the electronic coaster 100. The biometric sensor 103 is at least one of a fingerprint sensor, iris recognition sensor, pulse monitor sensor, voice detection sensor, gesture monitoring sensor, Echo Cardiograph (ECG) based sensors, pressure pattern sensor, etc.

The present disclosure shows a user interface 104 integrated with the electronic coaster 100. The user interface 104 helps receive one or more inputs from the user and display information to the user.

Figure 3:
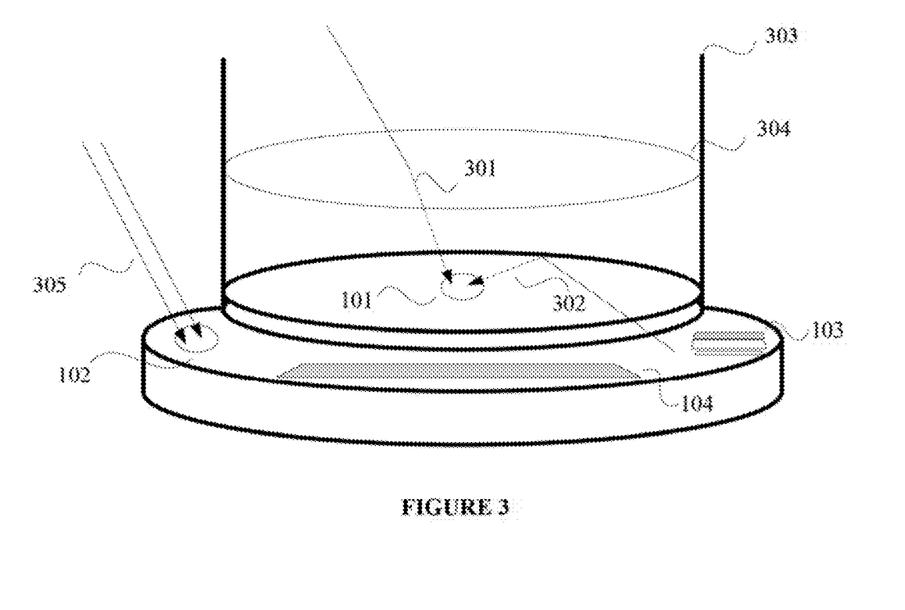
FIG. 3 shows an exemplary three-dimensional view of structure of an electronic coaster in accordance with some embodiments of the present disclosure.

FIG. 3 of the present disclosure shows an exemplary three-dimensional structure of an electronic coaster 100 in accordance with some embodiments of the present disclosure. As shown in figure, the at least first imaging sensor 101 is provisioned to capture at least one first image of the beverage 304 present in the beverage holder 303 placed on the electronic coaster 100. The at least first imaging sensor 101 detects light waves refracted 301 and reflected 302 by the beverage 304. The detected light waves help in capturing at least one first image of the beverage 304. The refracted 301 and reflected 302 light waves also comprise ambience light waves 305, which may reduce accuracy of beverage identification. In order to reduce ambient noise, the at least one second imaging sensor 102 is used. The at least one second imaging sensor 102 is configured to detect the ambient light waves 305. The at least one second imaging sensor 102 captures at least one second image of ambience around the beverage holder 303. Further, the computing unit 105 receives the at least one first and second image to determine spectral signature of the beverage 304. Upon determining the spectral signature, the computing unit 105 then compares the determined spectral signature with the predefined spectral signature of plurality of beverages to identify the type of beverage 304.

Figure 4:
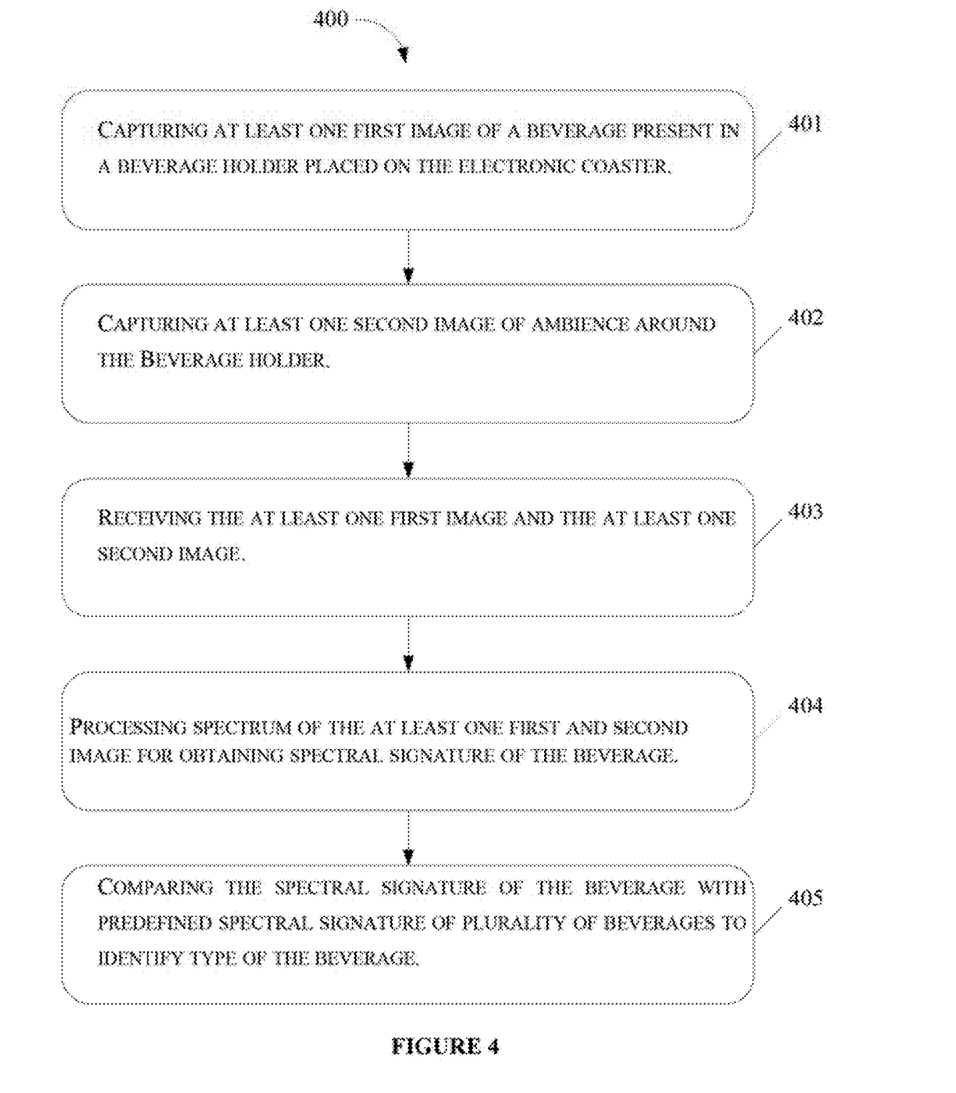
FIG. 4 shows an exemplary flow chart illustrating a method for identifying a beverage type by an electronic coaster.

FIG. 4 shows a flowchart illustrating a method for identifying a beverage 304 by an electronic coaster 100, in accordance with some embodiments of the present disclosure.

As illustrated in FIG. 4, the method 400 may comprise one or more steps to identify a beverage 304 by an electronic coaster 100. The method 400 may be described in the general context of computer executable instructions. Generally, computer executable instructions can include routines, programs, objects, components, data structures, procedures, modules, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At step 401, capture at least one first image of a beverage 304 present in a beverage holder 303 placed on the electronic coaster 100. The at least one first imaging sensor 101 is placed beneath the beverage holder 303 to capture at least one first image of the beverage 304 present in the beverage holder 303. The at least one first imaging sensor 101 detects light waves refracted 301 and reflected 302 by the beverage 304 and captures at least one first image of the beverage 304.

At step 402, capture at least one second image of ambience around the beverage holder 303. The at least one second image of the ambience around the beverage holder 303 is captured by the at least one second imaging sensor 102. The at least one second imaging sensor 102 is used to reduce ambient noise from the spectrum of the at least one first image.

At step 403, receive the at least one first and second image, by the computing unit 105. The computing unit 105 receives the at least one first and second image from the at least one first imaging sensor 101 and the at least one second imaging sensor 102 respectively. The computing unit 105 determines a light spectrum of the at least one first and second image to perform spectrum analysis on the images.

At step 404, process the spectrum of the at least one first image and the at least one second image respectively, to obtain spectral signature of the beverage 304. The computing unit 105 subtracts the spectrum of the at least one second image from the spectrum of the at least one first image, to alleviate the ambient noise. Upon deriving a noise free spectrum of the at least one first image of the beverage 304, the computing unit 105 processes the spectrum to obtain a spectral signature of the beverage 304.

In an embodiment, the at least one image represents a narrow wavelength range of electromagnetic spectrum. The computing unit 105 receives the at least one first and second image from the at least one first imaging sensor 101 and the at least one second imaging sensor 102. Further, the computing unit 105 combines the at least one first and second image to form a three dimensional hyper spectral data cube, also known as spectral signature.

At step 405, compare the spectral signature of the beverage 304 with predefined spectral signature of plurality of beverages. In an embodiment, the spectral signature of plurality of beverages is stored in the database 107. The obtained spectral signature of the beverage 304 is then compared with the predefined spectral signature of the plurality of beverages to identify the type of beverage.

In an embodiment, the identified beverage type is transmitted to the one or more devices 106 communicatively associated with the electronic coaster 100, by the computing unit 105. In an embodiment, the identified beverage type is displayed to the user through the user interface 104.

In an embodiment, a user can register with the electronic coaster 100 using the user interface 104 configured in the electronic coaster 100. When the user approaches the electronic coaster 100, the user interface 104 prompts the user for registration. Here, the user inputs the registration details. The registration details may include, but is not limited to, users' name, a password, address of residence, health condition, allergies, age, height, weight, etc. The registration details corresponding to the user are stored in the database 107 associated with the electronic coaster 100.

In an embodiment, the biometric sensor 103 configured in the electronic coaster 100 identifies a user associated with the electronic coaster 100. In an embodiment, during registration the user may produce at least one biometric sample. The at least one biometric sample may include, but is not limited to finger print, image of iris, pulse sample, voice sample, etc. The at least one biometric sample is stored in the database 107 along with the registration details corresponding to the user. During the user's subsequent visit, the electronic coaster 100 may identify the user using the biometric sensor 103 and the registration details. In an embodiment, a user may opt not to register with the electronic coaster 100.

In an embodiment, the user can also input other details during registration, which include, but are not limited to choice of beverages, budget, emergency contact number and preferred amount of beverage. The user inputs are also stored in the database 107. Upon identifying the user by the biometric sensor 103, the electronic coaster 100 may suggest the user a beverage through the user interface 104, based on the registration details and the other inputs provided by the user. The electronic coaster 100 may also suggest amount of beverage to be consumed by the user based on the data stored in the database 107. Also, the electronic coaster may suggest a beverage based on the height, weight and age of the user.

In an embodiment, the electronic coaster 100 may suggest the user, one or more beverages based on the registration details. Here, the electronic coaster 100 coaster fetches the one or more beverages from the database 107 based on the budget of the user's choice.

In an embodiment, the database 107 is configured with details of at least one of type of beverage, brand name, calorific value, presence of alcohol content in the beverage, presence of sugar content in the beverage, price and reference image.

In an embodiment, the electronic coaster 100 may estimate an average rate of sale of each beverage type based on the number of times each of the beverage type is identified.

Further, the estimated rate of sale may be used for statistical analysis of total sales of each beverage type.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise. The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 4, shows certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Figure 5:
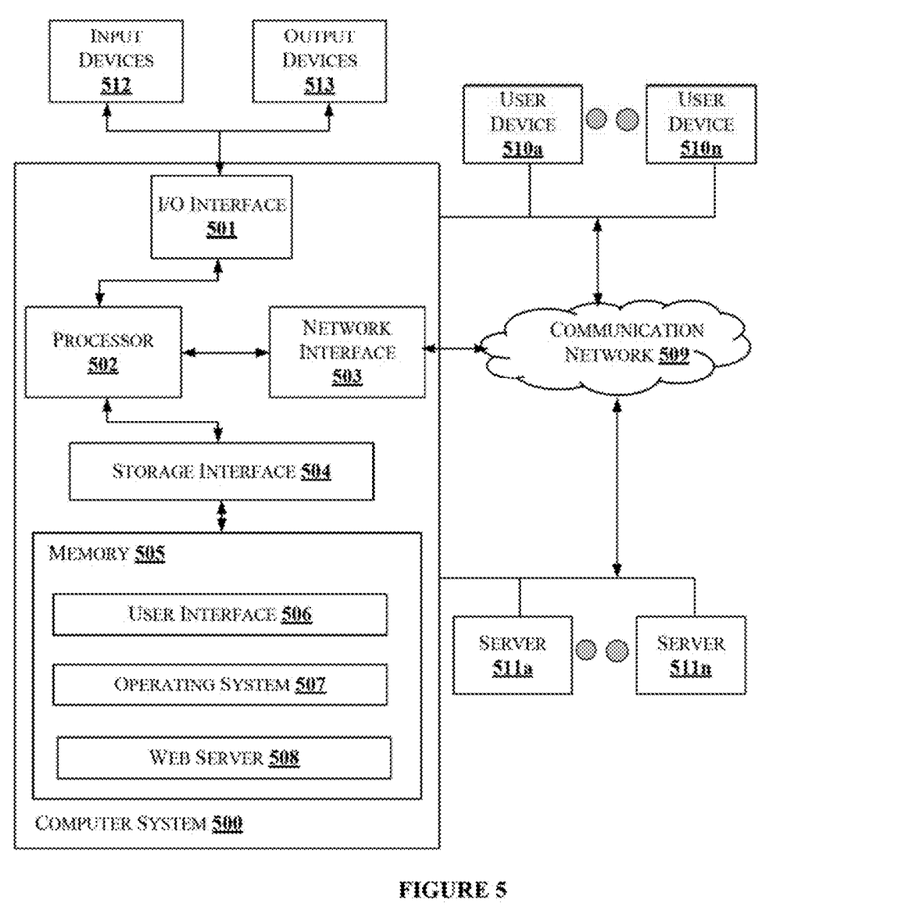
FIG. 5 shows an exemplary block diagram of a general computer system in accordance with some other embodiments of the present disclosure.

FIG. 5 illustrates a block diagram of an exemplary computer system 500 for implementing embodiments consistent with the present disclosure. In an embodiment, the computer system 500 is used in the electronic coaster 100. The computer system 500 may comprise a central processing unit ("CPU" or "processor") 502. The processor 502 may include specialized processing units such as integrated system (bus) controllers, memory management control units, floating point units, graphics processing units, digital signal processing units, etc.

The processor 502 may be disposed in communication with one or more input/output (I/O) devices 106 via I/O interface 501. The I/O interface 501 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the 1/O interface 501, the computer system 500 may communicate with one or more I/O devices 106. For example, the input device may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 500 is connected to the one or more user devices 510a . . . 510n and the one or more servers 511a . . . 511n through a communication network 509. The processor 502 may be disposed in communication with the communication network 509 via a network interface 503. The network interface 503 may communicate with the communication network 509. The network interface 503 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 509 may include, without limitation, a direct interconnection, local area network (LAN), wide area network (WAN), wireless network (e.g., using Wireless Application Protocol), the Internet, etc. Using the network interface 503 and the communication network 509, the computer system 500 may communicate with the one or more user devices 510a . . . 510n and the one or more servers 511a . . . 511n. The network interface 503 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 509 includes, but is not limited to, a direct interconnection, an e-commerce network, a peer to peer (P2P) network, local area network (LAN), wide area network (WAN), wireless network (e.g., using Wireless Application Protocol), the Internet, Wi-Fi and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 502 may be disposed in communication with a memory 505 (e.g., RAM, ROM, etc. not shown in FIG. 5) via a storage interface 504. The storage interface 504 may connect to memory 505 including, without limitation, memory drives, removable disc drives, etc., employing connection protocols such as serial advanced technology attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 505 may store a collection of program or database components, including, without limitation, user interface 506, an operating system 507, web server 508 etc. In some embodiments, computer system 500 may store user/application data 506, such as the data, variables, records, etc. as described in this disclosure. Such databases may be implemented as fault-tolerant, relational, scalable, secure databases such as Oracle or Sybase.

The operating system 507 may facilitate resource management and operation of the computer system 500. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like.

In some embodiments, the computer system 500 may implement a web browser 507 stored program component. The web browser 508 may be a hypertext viewing application, such as Microsoft Internet Explorer, Google Chrome, Mozilla Firefox, Apple Safari, etc. Secure web browsing may be provided using Secure Hypertext Transport Protocol (HTTPS), Secure Sockets Layer (SSL), Transport Layer Security (TLS), etc. Web browsers 508 may utilize facilities such as AJAX, DHTML, Adobe Flash, JavaScript, Java, Application Programming Interfaces (APIs), etc. In some embodiments, the computer system 500 may implement a mail server stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 500 may implement a mail client stored program component. The mail client may be a mail viewing application, such as Apple Mail, Microsoft Entourage, Microsoft Outlook, Mozilla Thunderbird, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

TECHNICAL ADVANTAGES

Embodiments of the present disclosure relate to an electronic coaster for identifying type of beverage present in a beverage holder placed on the electronic coaster. This disclosure illustrates a method and a device for identifying a beverage by performing spectral analysis of an image of the beverage.

In an embodiment of the present disclosure, the electronic coaster transmits the identified beverage type to a device. A concerned personnel associated with the device can access the beverage type and take necessary measures.

In an embodiment, the present disclosure illustrates a method and a device for enabling timely service to one or more users consuming a beverage. Here, an attendant is notified of the identified beverage thereby the attendant can provide service according to the identified beverage and one or more inputs provided by the user during registration.

In an embodiment, the disclosure provides a method and a device to intelligently identify a beverage placed in a beverage holder and suggests a similar beverage type upon completion of the beverage by the user.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

| REFERRAL NUMERALS | |
|---|---|
| Reference number | Description |
| 100 | Electronic coaster |
| 101 | First imaging sensor |
| 102 | Second imaging sensor |
| 103 | Biometric sensor |
| 104 | User interface |
| 105 | Computing unit |
| 106 | Devices |
| 107 | Database |
| 500 | Generic computer system |
| 501 | Input output interface |
| 502 | Processor |
| 503 | Network interface |
| 504 | Storage interface |
| 505 | Memory |
| 506 | User interface |
| 507 | Operating system |
| 508 | Web server |
| 509 | Communication network |
| 510a . . . 510n | User device |
| 511a . . . 511n | Server |
| 512 | Input devices |
| 513 | Output devices |

What is claimed is:

1. An electronic coaster, comprising:
   at least one first imaging sensor to capture at least one first image of a beverage present in a beverage holder placed on the electronic coaster;
   at least one second imaging sensor to capture at least one second image of ambience around the electronic coaster;
   and
   a computing unit to:
      receive the at least one first image and the at least one second image;
      process spectrum of the at least one first and second image for obtaining spectral signature of the beverage; and compare the spectral signature of the beverage with predefined spectral signature of plurality of beverages to identify type of the beverage.

2. The electronic coaster as claimed in claim 1, wherein the spectrum of the at least one second image is used to reduce ambient noise from the spectrum of the at least one first image.

3. The electronic coaster as claimed in claim 1, wherein the predefined spectral signature of plurality of beverages is stored in a database accessible by the electronic coaster.

4. The electronic coaster as claimed in claim 1 further comprising at least one biometric sensor to identify one or more users associated with the electronic coaster.

5. The electronic coaster as claimed in claim 1 further comprising a user interface to:
   display information to one or more users; and
   receive one or more inputs from the one or more users.

6. The electronic coaster as claimed in claim 1, wherein the at least one second imaging sensor detects light waves due to ambient lighting and environment around the beverage holder.

7. The electronic coaster as claimed in claim 1, wherein the at least one first imaging sensor detects light waves reflected and refracted through the beverage.

8. The electronic coaster as claimed in claim 1, wherein the computing unit is further configured to transmit the type of beverage to a device.

9. A method for identifying a beverage by an electronic coaster, comprising:
   capturing, by at least one first imaging sensor, at least one first image of a beverage present in a beverage holder placed on the electronic coaster;
   capturing, by at least one second imaging sensor, at least one second image of ambience around the electronic coaster;
   receiving, by a computing unit, the at least one first image and the at least one second image;
   processing, by the computing unit, spectrum of the at least one first and second image for obtaining spectral signature of the beverage; and
   comparing, by the computing unit, the spectral signature of the beverage with predefined spectral signature of plurality of beverages to identify type of the beverage.

10. The method as claimed in claim 9, wherein the spectrum of the at least one second image is used to reduce ambient noise from the spectrum of the at least one first image.

11. The method as claimed in claim 9, wherein the spectral signature of plurality of beverages is stored in a database accessible by the electronic coaster.

12. The method as claimed in claim 9 further comprising identifying one or more users associated with the electronic coaster by at least one biometric sensor.

13. The method as claimed in claim 9, further comprising:
   displaying, by a user interface, information to one or more users; and
   receiving, by the user interface, one or more inputs from the one or more users.

14. The method as claimed in claim 9, wherein the at least one second imaging sensor detects light waves due to ambient lighting and environment around the beverage holder.

15. The method as claimed in claim 9, wherein the at least one first imaging sensor detects light waves reflected and refracted through the beverage.

16. The method as claimed in claim 9, wherein the computing unit is further configured to transmit the type of beverage to a device.

* * * * *